United States Patent
Sims

[11] Patent Number: 5,087,255
[45] Date of Patent: Feb. 11, 1992

[54] ABSORBENT ARTICLE HAVING INFLECTED BARRIER CUFFS

[75] Inventor: Bret A. Sims, Villa Hills, Ky.

[73] Assignee: The Procter & Gamble Company, Cincinnati, Ohio

[21] Appl. No.: 561,475

[22] Filed: Aug. 1, 1990

Related U.S. Application Data

[63] Continuation of Ser. No. 288,045, Dec. 21, 1988, abandoned.

[51] Int. Cl.$^5$ .............................................. A61F 13/00
[52] U.S. Cl. ................................ 604/385.1; 604/385.2
[58] Field of Search ............................ 604/385.1, 385.2

[56] References Cited

U.S. PATENT DOCUMENTS

| | | | |
|---|---|---|---|
| 4,319,572 | 3/1982 | Widlund et al. | 604/385.2 |
| 4,657,539 | 4/1987 | Hasse | 604/385.2 |
| 4,695,278 | 9/1987 | Lawson . | |
| 4,704,115 | 11/1987 | Buell . | |
| 4,704,116 | 11/1987 | Enloe . | |
| 4,738,677 | 4/1988 | Foreman . | |
| 4,743,246 | 5/1988 | Lawson . | |
| 4,753,646 | 6/1988 | Enloe . | |
| 4,795,454 | 1/1989 | Dragoo . | |
| 4,808,178 | 1/1989 | Aziz et al. . | |
| 4,822,435 | 4/1989 | Igaue et al. | 604/385.2 X |
| 4,834,740 | 5/1989 | Suzuki et al. | 604/385.2 |
| 4,904,251 | 2/1990 | Igaue et al. . | |

FOREIGN PATENT DOCUMENTS

2196834A 5/1988 United Kingdom .
2197181A 5/1988 United Kingdom .

Primary Examiner—Richard J. Apley
Assistant Examiner—Rachel M. Healey
Attorney, Agent, or Firm—Steven W. Miller; Jeffrey V. Bamber; Richard C. Witte

[57] ABSTRACT

An absorbent article having an inflected barrier cuff which promotes better containment and fit. The absorbent article comprises a liquid pervious topsheet; a liquid impervious backsheet; an absorbent core positioned between the topsheet and the backsheet; a barrier cuff positioned adjacent each longitudinal edge of the absorbent article and having a proximal edge and a distal edge; spacing means for spacing the distal edge away from the liquid-receiving surface (topsheet) of the absorbent article; first closing means for securing the distal edges inboard of the proximal edges in a first waist region; and a second closing means for securing the distal edges outboard of the proximal edges in a second waist region. Because the distal edge is secured both inboard and outboard of the proximal edges, the barrier cuff is inflected such that the flipped out portion of the barrier cuff provides a gasketing action about the buttocks of the wearer to contain exudates and to provide a snug fit while the stand-up portion of the barrier cuff provides a channel to contain, restrain and hold body exudates.

6 Claims, 1 Drawing Sheet

ABSORBENT ARTICLE HAVING INFLECTED BARRIER CUFFS

This is a continuation of application Ser. No. 288,045, filed on Dec. 21, 1988, now abandoned.

FIELD OF THE INVENTION

The present invention relates to absorbent articles such as disposable diapers, and more particularly, to absorbent articles having barrier cuffs which improve the containment characteristics and fit of the absorbent article.

BACKGROUND OF THE INVENTION

The major function of absorbent articles such as disposable diapers and incontinent briefs or undergarments is to absorb and contain body exudates. Such articles are thus intended to prevent body exudates from soiling, wetting, or otherwise contaminating clothing or other articles, such as bedding, that come in contact with the wearer. The most common mode of failure for such products occurs when body exudates leak out of the gaps between the article and the wearer's leg or waist to adjacent clothing because they are not immediately absorbed within the article and the absorbent article is not able to sustain a good fit on the wearer such that gaps are created allowing the exudates to leak out of the chassis of the absorbent article. For example, urine tends to be deposited onto the topsheet in gushes such that the urine migrates to the gaps in the chassis where it can come in contact with clothing or other articles and be absorbed by these articles. Additionally, loose fecal material that is not easily absorbed by the absorbent article tends to "float" on the liquid-receiving surface and work its way past the gaps in the article in the legs or waist of the wearer.

Contemporary disposable diapers have a topsheet, a backsheet, an absorbent core, and elasticized leg flaps generally formed from an elastic member being enclosed in the continuous topsheet and backsheet which extend beyond the edges of the absorbent core. These elasticized leg flaps prove effective generally to prevent wicking and overflow from the fluid laden diaper to clothing contacting the edges of the diaper in that the elasticized leg flaps present a fluid impervious barrier between the edge of the diaper and the contacting clothing, and in addition, provide a gasketing action about the legs of the wearer to maintain a seal about the leg and minimize gapping. However, leakage along the perimeter of the diaper may still occur. As the diaper is worn for longer periods of time, forces tend to act on the diaper to degrade the initial fit on the wearer. Large gaps and sagging of the diaper in the legs and waist are formed by the degradation in fit. Thus, as liquids are deposited onto the topsheet, some of the liquid is not immediately absorbed through the topsheet and migrates toward the edges of the diaper where it can leak through or past the gaps in the diaper and come in contact with clothing or undergarments where it can be absorbed by and wicked into such garments.

Disposable diapers may be provided with barrier cuffs which inhibit loose fecal material or gushes of urine or liquids from soiling the wearer's clothing. The barrier cuffs restrain the free flow of this material and provide a structure to hold such material within the diaper so that as such material freely floats or flows on the topsheet of the diaper, it is contained within the diaper. Despite the effectiveness of such structures in containing such material, it has been found that liquids can leak beyond the barrier cuffs and soil the wearer's clothing because the diaper construction does not promote a sustained fit of the diaper on the wearer. Additionally, the barrier cuffs may not be properly applied to the wearer such that good initial fit is not achieved and the sustained fit is often worse.

Therefore, it is an object of the present invention to provide an absorbent article which has improved liquid containment characteristics.

It is an additional object of the present invention to provide an absorbent article having a barrier cuff which acts as a restraint against the leakage of body exudates.

It is a further object of the present invention to provide an absorbent article having a barrier cuff that consistently provides excellent initial and sustained fit.

It is also an object of the present invention to provide an absorbent article having a barrier cuff that minimizes fit degradation.

It is a still further object of the present invention to provide an absorbent article that is easy to apply to the wearer and promotes better containment by being less sensitive to variations in the application of the diaper.

These and other objects of the invention will be more readily apparent when considered in reference to the following description and when taken in connection with the accompanying drawings.

SUMMARY OF THE INVENTION

In accordance with the present invention, a disposable absorbent article such as a diaper is provided with a liquid pervious topsheet; a liquid impervious backsheet associated with the topsheet; an absorbent core positioned between the topsheet and the backsheet; a barrier cuff positioned adjacent each longitudinal edge of the absorbent article and having a proximal edge and a distal edge; spacing means for spacing the distal edges away from the liquid-receiving surface so as to enhance the containment characteristics of the barrier cuffs; first closing means for securing the distal edges of the barrier cuffs to the absorbent article inboard of the proximal edges in the first waist region of the absorbent article; and second closing means for securing the distal edges of the barrier cuffs to the absorbent article outboard of the proximal edges in the second waist region so that the distal edges are "flipped out" to form inflected barrier cuffs which improve the containment and fit of the diaper.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

Figure 1:
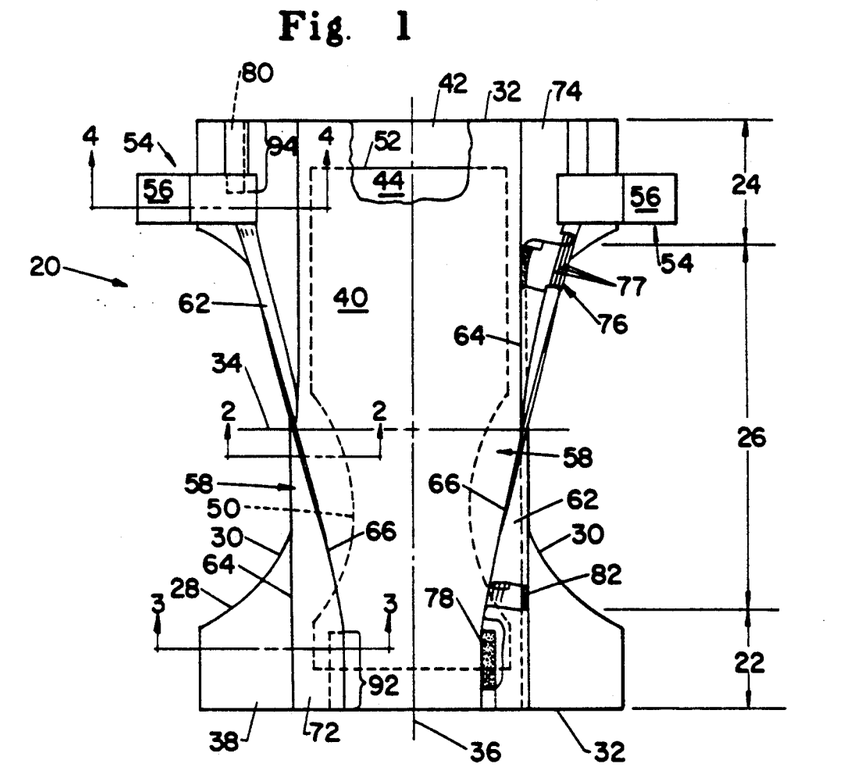
FIG. 1 is a plan view of a disposable diaper embodiment of the present invention having portions cut-away to reveal underlying structure.

As used herein, the term "absorbent article" refers to articles which absorb and contain body exudates and more specifically refers to articles which are placed against or in proximity to the body of the wearer to absorb and contain the various exudates discharged from the body. Absorbent articles are typically differentiated by whether they are reusable or disposable. Disposable absorbent articles refers to articles which are intended to be discarded after a single use (i.e., they are not intended to be laundered or otherwise restored or reused). The absorbent articles of the present invention are preferably disposable absorbent articles. The absorbent articles may be further defined by whether they are "unitary" such that they do not require separate manipulative parts or whether they comprise an element of a diaper system such as a separate holder and liner. The absorbent articles of the present invention are preferably unitary. A preferred embodiment of a unitary disposable absorbent article of the present invention, diaper 20, is shown in FIG. 1. As used herein, the term "diaper" refers to a garment generally worn by infants and incontinent persons that is worn about the lower torso of the wearer. It should be understood, however, that the present invention is also applicable to other disposable absorbent articles such as incontinent briefs or undergarments, disposable training pants, diaper holders, sanitary napkins, and the like.

FIG. 1 is a plan view of the diaper 20 of the present invention in its flat-out, uncontracted state (i.e., with all elastic induced contraction pulled out) with portions of the structure being cut-away to more clearly show the construction of the diaper 20 and with the portion of the diaper 20 which contacts the wearer facing the viewer. The diaper 20 is shown in FIG. 1 to have a first waist region 22, a second waist region 24, a crotch region 26, and a periphery 28 which is defined by the outer edges of the diaper 20 in which the longitudinal edges are designated 30 and the end edges are designated 32. The diaper 20 additionally has a lateral centerline which is designated 34 and a longitudinal centerline which is designated 36.

The diaper 20 comprises a liquid pervious topsheet 38, the liquid-receiving surface of the diaper 20 being generally defined by the topsheet 38 and being designated 40; a liquid impervious backsheet 42; an absorbent core 44 having a garment surface 46, a body surface 48, and edges that are designated side edges 50 and waist edges 52; fastening means 54 for securing the diaper on the wearer such as the pair of tape tab fasteners 56; a side flap 58 extending outwardly from each side edge 50 of the absorbent core 44 in at least the crotch region 26; barrier cuffs 62 each having a proximal edge 64, a distal edge 66, a first end 72, and a second end 74; spacing means 76 such as elastic members 77 for spacing the distal edge 66 away from the liquid-receiving surface 40; first closing means 78 for securing a portion of the distal edge 66 inboard of the proximal edge 64; and second closing means 80 for securing a portion of the distal edge 66 outboard of the proximal edge 64.

FIG. 1 shows a preferred embodiment of the diaper 20 in which the backsheet 42 has length and width dimensions generally larger than those of the absorbent core 44. The backsheet 42 extends beyond the edges of the absorbent core 44 to thereby form the periphery 28 of the diaper 20. The periphery 28 defines the outer perimeter or, in other words, the edges of the diaper 20. The periphery 28 comprises the longitudinal edges 30 and the end edges 32. As shown in FIG. 1, the topsheet 38 is generally coterminous with the backsheet 42 along at least the end edges 32 and preferably the longitudinal edges 30.

The diaper 20 has a first waist region 22 and a second waist region 24 extending, respectively, from the end edges 32 of the diaper periphery 28 toward the lateral centerline 34 of the diaper 20 a distance up to about $\frac{1}{2}$, preferably from about $\frac{1}{8}$ to about $\frac{1}{4}$, of the length of the diaper 20. The waist regions generally comprise those portions of the diaper 20 which, when worn, encircle the waist of the wearer. The crotch region 26 is that portion of the diaper 20 positioned between the first waist region 22 and the second waist region 24, and comprises that portion of the diaper 20 which, when worn, is positioned between the legs of the wearer and covers the lower torso of the wearer.

Figure 2:
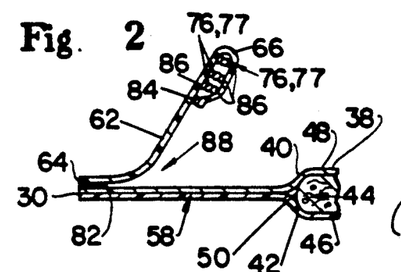
FIG. 2 is a fragmentary sectional view taken along section line 2—2 of FIG. 1.

FIG. 2 is fragmentary sectional view taken along line 2—2 of FIG. 1 and depicts a preferred diaper construction in the crotch region 26 of the diaper 20. The absorbent core 44 is disposed between the topsheet 38 and the backsheet 42; the topsheet 38 and the backsheet 42 extend beyond the side edge 50 of the absorbent core 44 to form the side flap 58. The barrier cuff 62 is preferably formed by joining portions of a separate barrier cuff member to the diaper 20 adjacent the longitudinal edge 30. The proximal edge 64 of the barrier cuff 62 is formed by joining a segment of the barrier cuff member to the diaper 20 by the seal means 82 such as an adhesive bead so as to form a seal along the proximal edge 64 to present a barrier to liquids wicking past the barrier cuffs. The distal edge 66 is preferably not secured to any underlying elements of the diaper 20 in the crotch region 26. As shown in FIG. 2, the distal edge 66 is formed by folding an end of the barrier cuff member back upon itself and securing it to another segment of the barrier cuff member by the distal attachment means 84 to form a hem. A spacing means 76, such as a plurality of elastic members 77, preferably the three elastic members 77 shown in FIG. 2, is enclosed in the hem that is formed in the distal edge 66 of the barrier cuff member; the elastic members 77 being operatively associated with the barrier cuff 62 by the elastic attachment means 86. The distal edge 66 is thus spaced away from the liquid-receiving surface 40 of the topsheet 38 by the elastic gathering action of the elastic members 77; a channel 88 thereby being formed between the proximal edge 64 and the distal edge 66. The channel 88 is shown as being open and ready to restrain, contain, and hold body exudates until the diaper 20 is removed from the wearer.

Figure 3:
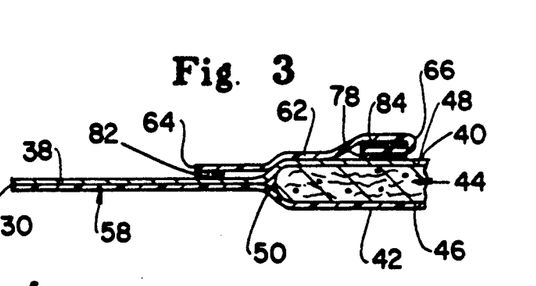
FIG. 3 is a fragmentary sectional view taken along section line 3—3 of FIG. 1.

FIG. 3 is a fragmentary sectional view taken along line 3—3 of FIG. 1 and depicts a preferred diaper construction in the first waist region 22 of the diaper 20. The topsheet 38 and the backsheet 42 extend beyond the side edge 50 of the absorbent core 44 to form the side flap 58. The barrier cuff 62 is formed by joining portions of a separate barrier cuff member to the topsheet 38. The proximal edge 64 is formed by joining a segment of the barrier cuff member to the underlying structure of the diaper 20 by the seal means 82 such as an adhesive bead. The distal edge 66 is secured inboard of the proximal edge 64 to the underlying structure (topsheet 38) of the diaper 20 by the first closing means 78, which preferably comprises an adhesive. Therefore, the distal edge 66 is closed (i.e., it is not open nor capable of being spaced away from the liquid-receiving surface 40). It should also be noted that the spacing means 76 is preferably not disposed in the first waist region 22 because the distal edge 66 is preferably secured closed and is not designed to be spaced away from the liquid-receiving surface 40 in the first waist region 22. The lack of gathering of the distal edge 66 adjacent the end edge 32 also tends to reduce the forces which tend to pull the diaper 20 downward resulting in sagging and gapping of the diaper 20 in the waist region. Although the channel 88 is not open to restrain the flow of body exudates in the first waist regions, it may act to contain and hold exudates which flow along the channel 88.

Figure 4:
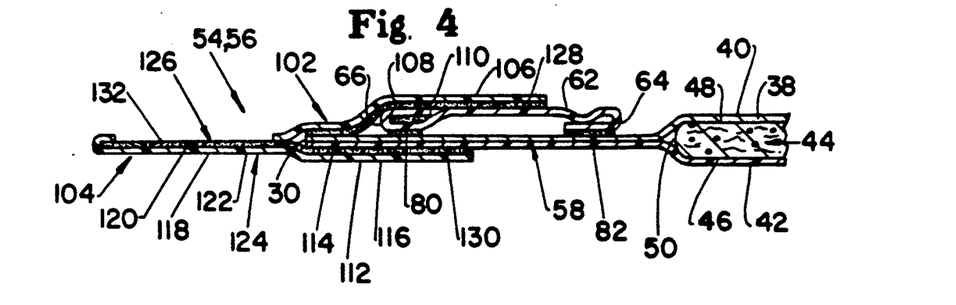
FIG. 4 is a fragmentary sectional view taken along section line 4—4 of FIG. 1.

FIG. 4 is a fragmentary sectional view taken along line 4—4 of FIG. 1 and depicts a preferred diaper construction in the second waist region 24 of the diaper 20. The topsheet 38 and the backsheet 42 extend beyond the side edge 50 of the absorbent core 44 to form the side flap 58. The barrier cuff 62 is formed by joining portions of a separate barrier cuff member to the side flap 58; i.e., the topsheet 38. The proximal edge 64 is formed by joining a segment of the barrier cuff member to the underlying structure of the diaper 20 by the seal means 82 such as an adhesive bead. The distal edge 66 is secured outboard of the proximal edge 64 to the underlying structure (topsheet 38) of the diaper 20 by the second closing means 80, which preferably comprises an adhesive. Therefore, the barrier cuff 62 is closed such that it is not capable of being spaced away from the liquid-receiving surface 40. It should also be noted that a spacing means 76 such as an elastic member 77 is preferably not disposed in the second waist region 24 because the distal edge 66 is preferably secured closed and is not designed to be spaced away from the liquid-receiving surface 40 in the second waist region 24.

The absorbent core 44 may be any means which is generally compressible, conformable, non-irritating to the wearer's skin, and capable of absorbing and retaining liquids and certain body exudates. A preferred absorbent core 44 has a garment surface 46 and a body surface 48.

The absorbent core 44 may be manufactured in a wide variety of sizes and shapes (e.g., rectangular, hourglass, asymmetric, etc.) and from a wide variety of liquid absorbent materials commonly used in disposable diapers and other absorbent articles, such as comminuted wood pulp which is generally referred to as airfelt. Examples of other suitable absorbent materials include creped cellulose wadding, absorbent foams, absorbent sponges, super absorbent polymers, absorbent gelling materials, or any equivalent materials or combination of materials. The total absorbent capacity of the absorbent core 44 should, however, be compatible with the design exudate loading in the intended use of the diaper 20. Further, the size and absorbent capacity of the absorbent core 44 may be varied to accommodate wearers ranging from infants through adults.

The absorbent core 44 may comprise a layer of absorbent material comprising hydrophilic fibers and particles of absorbent gelling material (hydrogel) such as the absorbent structure described in U.S. Pat. No. 4,610,678 entitled "High-Density Absorbent Structure" which issued to Paul T. Wiseman and Steven A. Goldman on Sept. 9, 1986 and which patent is incorporated herein by reference. A preferred embodiment of the absorbent core 44 is a dual-layered absorbent core in a preferred configuration such as is generally described in U.S. Pat. No. 4,673,402 entitled "Absorbent Article With Dual-Layered Cores" which issued to Paul T. Wiseman, Dawn I. Houghton and Dale A. Gellert on June 16, 1987, and which is incorporated herein by reference, having an asymmetric-shaped upper layer and a lower layer. Another exemplary embodiment of an absorbent core useful in the present invention is described in European Patent Application EP-A-254,476; The Procter & Gamble Company; published Jan. 27, 1988, which discloses absorbent members having a storage zone and an acquisition zone having a lower average density and a lower average basis weight per unit area than the storage zone so that the acquisition zone may effectively and efficiently rapidly acquire discharged liquid. This European patent application is hereby incorporated herein by reference.

A preferred embodiment of the diaper 20 shown in FIG. 1 has an hourglass-shaped absorbent core 44 and is intended to be worn by infants ranging in weight from about 5 kgs to about 12 kgs (about 12 pounds to about 26 pounds). It should be understood, however, that the size, shape, configuration, and total absorbent capacity of the absorbent core 44 may be varied to accommodate wearers ranging from infants through adults. Therefore, the dimensions, shape, and configuration of the absorbent core 44 may be varied (e.g., the absorbent core may have a varying caliper, or a hydrophilic gradient, a capillarity differential, low density zones, or may or may not contain absorbent gelling materials). The absorbent core 44 is preferably a batt of airfelt and absorbent gelling material about 32 cm wide (lateral dimension), about 45 cm long (longitudinal dimension) and approximately 7 cm across the narrowest part of the crotch region.

The backsheet 42 is positioned adjacent the garment surface 46 of the absorbent core 44 and is preferably secured thereto by core attachment means (not shown) such as those well known in the art. For example, the backsheet 42 may be secured to the absorbent core 44 by a uniform continuous layer of adhesive, a patterned layer of adhesive, or an array of separate lines or spots of adhesive. Adhesives which have been found to be satisfactory are manufactured by Eastman Chemical Products Company of Kingsport, Tennessee and marketed under the trade name Eastobond A-3 and by Century Adhesives, Inc. of Columbus, Ohio and marketed under the trade name Century 5227. The core attachment means preferably comprise an open pattern network of filaments of adhesive as is shown in U.S. Pat. No. 4,573,986 entitled "Disposable Waste-Containment Garment" which issued to J. A. Minetola and David R. Tucker on Mar. 4, 1986, and which is incorporated herein by reference.

The backsheet 42 is impervious to liquids and is preferably manufactured from a thin plastic film, although other flexible liquid impervious materials may also be used. The backsheet 42 prevents the exudates absorbed and contained in the absorbent core 44 from wetting articles which contact the diaper 20 such as bedsheets and undergarments. Preferably, the backsheet 42 is a polyethylene film having a thickness of from about 0.012 mm (0.5 mil) to about 0.051 cm (2.0 mils), although other flexible, liquid impervious materials may be used. As used herein, the term "flexible" refers to materials which are compliant and which will readily conform to the general shape and contours of the human body.

A suitable polyethylene film is manufactured by Monsanto Chemical Corporation and marketed in the trade as Film No. 8020. The backsheet 42 is preferably embossed and/or matte finished to provide a more clothlike appearance. Further, the backsheet 42 may permit vapors to escape from the absorbent core 44 while still preventing exudates from passing through the backsheet 42.

The size of the backsheet 42 is dictated by the size of the absorbent core 44 and the exact diaper design selected. In a preferred embodiment, the backsheet 42 has a modified hourglass shape extending beyond the absorbent core 44 a minimum distance of at least about 1.3 cm to about 2.5 cm (about 0.5 to about 1.0 inch) around the entire diaper periphery 28.

The topsheet 38 is compliant, soft feeling, and non-irritating to the wearer's skin. Further, the topsheet 38 is liquid pervious permitting liquids to readily penetrate through its thickness. A suitable topsheet may be manufactured from a wide range of materials, such as porous foams, reticulated foams, apertured plastic films, natural fibers (e.g., wood or cotton fibers), synthetic fibers (e.g., polyester or polypropylene fibers) or from a combination of natural and synthetic fibers. Preferably, it is made of a hydrophobic material to isolate the wearer's skin from liquids in the absorbent core 44.

A preferred topsheet 38 comprises staple length polypropylene fibers having a denier of about 1.5, such as Hercules Type 151 polypropylene marketed by Hercules, Inc. of Wilmington, Delaware. As used herein, the term "staple length fibers" refers to those fibers having a length of at least about 15.9 mm (0.625 inches).

There are a number of manufacturing techniques which may be used to manufacture the topsheet 38. For example, the topsheet 38 may be woven, non-woven, spunbonded, carded, or the like. A preferred topsheet 38 is carded, and thermally bonded by means well known to those skilled in the fabrics art. Preferably, the topsheet 38 has a weight from about 18 to about 25 grams per square meter, a minimum dry tensile strength of at least about 400 grams per centimeter in the machine direction and a wet tensile strength of at least about 55 grams per centimeter in the cross machine direction.

The topsheet 38 and the backsheet 42 are associated together in any suitable manner as is well known in the diaper manufacturing art. As used herein, the term "associated" encompasses configurations whereby the topsheet 38 is directly joined to the backsheet 42 by affixing the topsheet 38 directly to the backsheet 42, and configurations whereby the topsheet 38 is indirectly joined to the backsheet 42 by affixing the topsheet 38 to intermediate members which in turn are affixed to the backsheet 42. In a preferred embodiment, the topsheet 38 and the backsheet 42 are joined directly to each other in the diaper periphery 28 by flap attachment means (not shown) such as an adhesive or any other attachment means as is known in the art. In general, the core attachment means that affixes the absorbent core 44 to the backsheet 42 is the same means as the flap attachment means that affixes the topsheet 38 to the backsheet 42. Thus, for example, a uniform continuous layer of adhesive, a patterned layer of adhesive, an array of separate lines or spots of adhesive, or a network of adhesive filaments such as shown in the above-referenced U.S. Pat. No. 4,573,986 may be used.

The side flaps 58 are that portion of the diaper 20 between the periphery 28 and the side edges 50 of the absorbent core 44. Thus, in a preferred embodiment of the present invention as shown in FIG. 1, the side flaps 58 are formed from the extension of the backsheet 42 and the topsheet 38 extending outwardly from and along the side edges 50 of the absorbent core 44 of the diaper 20 in at least the crotch region 26.

The diaper 20 is provided with a fastening means 54 for forming a side closure in the diaper 20. Thus, the diaper 20 is fitted to the wearer and preferably the first waist region 22 and the second waist region 24 are maintained in an overlapping configuration when the diaper 20 is worn. While the fastening means 54 may comprise any of a number of fastening systems as are known in the art such as belts or inner fastening members, in a preferred embodiment of the present invention as shown in FIG. 1, the fastening means 54 comprises a tape tab 56 disposed adjacent each longitudinal edge 30 of the diaper 20 preferably in the second waist region 24. Tape tab fasteners 54 are preferably applied to the second waist region 24 of the diaper 20 to provide a fastening means to hold the diaper to the wearer, although they may alternatively be disposed in the first waist region 22. The tape tab fasteners 54 can be any of those tape tabs well known in the art, such as the adhesive fastening tape tabs disclosed in U.S. Pat. No. 3,848,594 entitled "Tape Fastening System For Disposable Diaper" issued to Kenneth B. Buell on Nov. 19, 1974, which patent is incorporated herein by reference.

The barrier cuffs 62 of the present invention provide a structure to restrain the free flow of body exudates along the liquid-receiving surface 40 and to hold and contain such exudates within the diaper 20 and to provide a gasketing action about the wearer. Each barrier cuff 62 is a flexible member having a proximal edge 64 and a distal edge 66. As used herein, the term "flexible" refers to materials which are compliant and will readily conform to the general shape and contours of the body. In addition, if the spacing means 76 comprises one or more elastic members 77, the barrier cuffs 62 must be contractible so that the distal edges 66 may be sufficiently spaced away from the liquid-receiving surface 40 to form the channel 88 and may provide a gasketing action about the buttocks of the wearer. The barrier cuffs 62 may be manufactured from a wide variety of materials such as polypropylene, polyester, rayon, nylon, foams, plastic films, formed films, elastic laminates and elastic foams. A number of manufacturing techniques may be used to manufacture the barrier cuffs. For example, the barrier cuffs 62 may be woven, non-woven, spunbonded, carded, or the like. A particularly preferred barrier cuff 62 comprises a laminate of a nonwoven polypropylene material secured to a liquid impermeable polyethylene film. The materials may be secured or laminated to each other by any method as is known in the art.

As shown in FIGS. 1 and 2, the barrier cuff 62, and more particularly, the proximal edge 64, is disposed adjacent to and preferably inboard of the longitudinal edge 30 of the diaper 20. The term "inboard" is defined as the direction toward the centerline (34 or 36, respectively) of the diaper 20 that is parallel to the respective edge of the diaper 20 along which the particular barrier cuff is disposed. The proximal edge 64 is preferably disposed inboard of the longitudinal edge 30 so that exudates, especially loose fecal material which is not easily absorbed and tends to float along the liquid-receiving surface 40, will contact the barrier cuff 62 before it can contact the edges of the diaper 20. Thus, the proximal edge 64 is preferably disposed between the longitudinal edge 30 and the longitudinal centerline 36 of the diaper 20. Most preferably, the proximal edge 64 is disposed between the longitudinal edge 30 and the side edge 50 of the absorbent core 44 in at least the crotch region 26 of the diaper 20. (It should be noted that if the side flaps 58 are elasticized by one or more flap elastic members to form a gasketing cuff adjacent each longitudinal edge 30, as is known in the art, then the proximal edge 64 is preferably positioned between the innermost flap elastic member and the side edge 50 of the absorbent core 44 in at least the crotch region 26.)

The proximal edges 64 and the distal edges 66 are in a spaced relation to each other and define the effective width of each of the barrier cuffs 62. The proximal edges 64 and the distal edges 66 may be in a parallel, nonparallel, rectilinear or curvilinear relationship. In addition, each of the barrier cuffs 62 may have a variety of different cross-sectional areas including circular, square, rectangular or any other shape such as that shown in FIGS. 2, 3 and 4. Preferably, the proximal edge 64 is spaced from the distal, edge 66 in a parallel and rectilinear relationship. The effective width of the barrier cuff is an important parameter in reducing leakage of body exudates out of the diaper 20. If the effective width of the barrier cuff is too small, then gaps will be formed between the leg of the wearer and the distal edge 66 such that liquids may flow over the distal edge 66 to the periphery 28 of the diaper 20. A preferred embodiment of the diaper 20 is intended to be worn by infants ranging in weight from about 5 kgs to about 12 kgs (about 12 pounds to about 26 pounds, and each barrier cuff 62 preferably has an effective width of at least about 25 mm (about 1 inch), preferably from about 25 mm (about 1 inch) to about 50 mm (about 2 inches), and most preferably about 38 mm (about 1½ inch). Of course, the effective width should be dimensionalized as the size of the wearer increases or decreases, particularly with adult wearers.

The distal edge 66 of each barrier cuff 62 is preferably not secured to any underlying elements of the diaper 20 in at least the crotch region 26 so that it may be spaced away from the liquid-receiving surface 40. The distal edge 66 is preferably spaced away from the liquid-receiving surface 40 so that the barrier cuff 62 may form a channel 88 to enhance the containment of the diaper 20. As used herein, "spaced" includes embodiments wherein the distal edges 66 may assume one or more positions relative to the liquid-receiving surface 40 including at some times assuming a position adjacent the liquid-receiving surface 40.

The distal edge 66 of each barrier cuff 62 is disposed inboard of the proximal edge 64 in the first waist region 22 so as to present a more effective barrier against the flow of exudates. The distal edges 66 are maintained inboard of the proximal edges 64 in the first waist region 22 by the first closing means 78 so as to obviate their inversion. As seen in FIGS. 1 and 3, in a preferred embodiment of the present invention, the first closing means 78 is located in a first closure zone 92 which is disposed inboard of the side flaps 58 and, in the same embodiment, or in another preferred embodiment of the present invention, at least a portion of the first closing means 78 is positioned above at least a portion of the absorbent core 44.

As shown in FIG. 1, the distal edges 66 are preferably laterally spaced apart from each other in the first waist region 22. However, the lateral spacing between the distal edges 66 can range from being crossed over each other to abutting each other to being laterally spaced apart up to the width of the proximal edges in the first waist region 22. Thus, in a preferred embodiment as shown in FIG. 1, the distal edges may be laterally spaced apart from about $-25$ mm ($-1$ inch) (overlapping edges) up to about 150 mm (6inches). Preferably, the distal edges 66 are spaced apart not greater than about 100 mm (about 4 inches) so that the barrier cuff will fit in the innermost leg crease of the wearer rather than ride along the wearer's outer thigh. Most preferably, the distal edges are spaced apart from about 75 mm (about 3 inches) to about 100 mm (about 4 inches) on a medium sized diaper, most preferably about 88 mm (about 3.5 inches).

The distal edges 66 are also shown in FIG. 1 to be disposed parallel to each other and perpendicular to the end edge 32 of the diaper 20 in the first waist region 22. While this is a preferred embodiment, the distal edges 66 may alternatively be angled toward or away from each other, preferably toward each other, such that the distal edges 66 are disposed non-perpendicular to the end edges 32. Angling the barrier cuffs relative to the end edge 32 may assist in allowing the barrier cuff to remain spaced from the liquid-receiving surface 40 in the crotch region 26 during use.

The distal edges 66 are preferably laterally spaced apart from each other in the crotch region 26. The lateral spacing of the distal edges 66 is especially important in the crotch region 26 to prevent body exudates, especially urine, from leaking out of the diaper 20 in the leg regions of the wearer. If the distal edges 66 are laterally spaced too far from each other, then the barrier cuffs 62 have an increased tendency to "flip out" in the crotch region 26 such that urine can flow over the barrier cuffs 62. If the distal edges 66 are spaced too close to each other, then the barrier cuffs 62 provide a reduced area for deposition of exudates such that exudates could be deposited directly onto the barrier cuffs 62 and flow to the edges of the diaper 20. Thus, the lateral spacing of the distal edges 66 in the crotch region 26, measured at the narrowest spacing of the distal edges 66 when the diaper 20 is placed into its flat-out, uncontracted state as shown in FIG. 1, should be at least about 1.5 times the effective width of the narrowest barrier cuff 62, typically each barrier cuff. Preferably, the lateral spacing of the distal edges 66 in the crotch region 26 should be between about 1.5 times and 4 times the effective width of the narrowest barrier cuff, most preferably about 2.3 times. Thus, in a preferred embodiment, the distal edges 66 are laterally spaced apart in the crotch region 26 at least about 63 mm (about 2.5 inches), preferably from about 75 mm (about 3 inches) to about 100 mm (about 4 inches), most preferably about 88 mm (about 3.5 inches). Of course, the lateral spacing should be dimensionalized as the size of the wearer increases or decreases, especially for adult wearers.

The distal edge 66 of each barrier cuff 62 is disposed outboard of each proximal edge 64 in the second waist region 24 of the diaper 20. The term "outboard" is defined as the direction away from the centerline of the diaper 20 that is parallel to the respective edge of the diaper 20 along which the barrier cuff is disposed. (i.e., the direction opposite from the direction defined by the term "inboard.") Thus, the barrier cuff 62 is "flipped out" in the second waist region 24. The flipped out portion of the barrier cuff promotes better containment that is less sensitive to application variations and provides a contoured fit about the buttocks of the wearer. The distal edges 66 are maintained outboard of the proximal edges 64 in the second waist region 24 by the second closing means 80.

As shown in FIG. 1, the distal edges 66 are laterally spaced apart from each other in the second waist region 24. However, the spacing between the distal edges 66 can range such that the distal edges are angled relative to each other. Thus, in a preferred embodiment as shown in FIG. 1, the distal edges may be spaced apart up to about 250 mm (10 inches), preferably from about 150 mm (6 inches) to about 200 mm (8 inches). The distal edges 66 are also shown in FIG. 1 to be disposed parallel to each other and perpendicular to the end edge 32 of the diaper 20. While this is a preferred embodiment, the distal edges 66 may alternatively be angled toward or away from each other, preferably away from each other, such that the distal edges are disposed non-perpendicular to the end edges.

Because the distal edge 66 is disposed inboard of the proximal edge 64 in the first waist region 22 and outboard of the proximal edge 64 in the second waist region 24, the distal edge 66 is inflected ("flipped out") along its length. This inflection transitions the barrier cuff from snugly fitting about the buttocks (the flipped out portion) to fitting in the "no motion" zone of the legs for better containment (the stand-up portion; i.e., the distal edge 66 being disposed inboard of the proximal edge 64). The resultant inflected barrier cuff is easier to apply to the wearer and ensures that the fit of the barrier cuff is in the "no motion" zone in the crotch region with a snug fit about the wearer's buttocks in at least the second waist region 24.

It has been found that the inflected barrier cuff thus provides both a gasketing action about the buttocks of the wearer to provide a snug fit which reduces leakage of body exudates, especially runny BM, and a stand-up barrier cuff in the crotch region 26 and the first waist region 22 to constrain, contain and hold body exudates within the diaper along the channel 88. However, it has been found that if the barrier cuff is "flipped out" too far toward the first waist region 22 along the length of the barrier cuff 62, then body exudates will tend to flow over the barrier cuffs. Thus, it is preferred that the inflected barrier cuffs, in use, provide a gasketing action about the buttocks of the wearer to provide a snug fit (i.e., the flipped out portion of the barrier cuffs is positioned) in less than about 50% of the length of the diaper, more preferably less than about 40% of the length of the diaper 20, and most preferably only in the second waist region 24. (The percent length of the flipped out portion is defined as that length of the diaper in which the barrier cuff is flipped out divided by the total length of the diaper times 100%.) Thus, the stand-up portion of the barrier cuff (distal edge 66 disposed inboard of the proximal edge 64) is provided, in use, in at least about 50% of the length of the diaper, preferably at least about 60% of the length of the diaper, and most preferably from the first waist region 22 to and throughout the crotch region 26.

The flipped out portion of the barrier cuff 62 can be maintained in less than about 50% of the length of the diaper in a number of different ways, For example, the second closure zone 94 is preferably longer than the first closure zone 92. Alternatively, a closure attachment means may be positioned on the barrier cuff 62 toward or in the crotch region 26 of the diaper for securing the distal edge 66 inboard of the proximal edge 64 so that the flipped out portion is maintained in less than about 50% of the length.

A channel 88 is formed between the proximal edge 64 and the distal edge 66 of the barrier cuff 62 in the crotch region 26 and the first waist region 22. The channel 88 forms a barrier to the flow of exudates as they tend to move or float across the topsheet 38. The channel 88 also contains and holds exudates within the diaper 20 until the diaper 20 can be removed.

The barrier cuffs 62 are preferably liquid impermeable so as to prevent the strikethrough of body exudates. A liquid impermeable barrier cuff 62 retards the movement of liquid through the barrier cuff 62, thereby making it more leakage resistant. The barrier cuffs 62 may be rendered liquid impermeable in any manner well known in the art such as selectively treating the barrier cuffs, untreating the barrier cuffs, by securing a separate material to the barrier cuffs or by choosing a material for the barrier cuffs that is liquid impermeable.

The barrier cuffs 62 may additionally be provided with absorbent means secured to or within the barrier cuff 62. The absorbent means absorb and contain exudates which contact the barrier cuff 62. The absorbent means may be any means which is capable of absorbing and retaining liquids and may have any size, shape, configuration or absorbent capacity. The absorbent means may be disposed in the barrier cuff 62 along the inboard surfaces of the barrier cuff 62 or within the barrier cuff 62.

A preferred embodiment of the diaper 20 shown in FIG. 1 is provided with each of the barrier cuffs 62 joined to the side flaps 58 of the diaper 20. The term "joined" includes any means for securing the barrier cuff 62 to the diaper 20, and includes embodiments wherein the barrier cuffs 62 are separate members directly or indirectly secured to the side flaps 58 (i.e., integral barrier cuffs) or embodiments wherein the barrier cuffs 62 are constructed from the same member or material as an element of the diaper 20 such as the side flap 58 so that the barrier cuffs 62 are a continuous and undivided element of the side flap 58 (i.e., unitary barrier cuffs). The barrier cuffs 62 may alternatively be joined to the backsheet 42, the topsheet 38, the absorbent core 44, or any combination of these or other elements of the diaper 20. In the preferred embodiment, the barrier cuffs 62 are joined with the side flaps 58 (directly to the portion of the topsheet 38 forming the side flap 58) by the seal means 82 such as adhesive to form the proximal edge 64, the distal edge 66 being formed by folding an end of the material back upon itself and being secured to another segment by the distal attachment means 84.

The proximal edges 64 and the side flaps 58 are joined together in any suitable manner. As used herein, the term "joined" encompasses configurations whereby the proximal edges 64 are directly secured to the side flap 58 by affixing the proximal edges 64 directly to the side flap 58 and configurations whereby the proximal edges 64 are indirectly secured to the side flap 58 by affixing the proximal edges 64 to intermediate members which in turn are affixed to the side flap 58. In a preferred embodiment, the proximal edges 64 and the side flaps 58 are directly secured to each other at least in the crotch region 26 by the seal means 82.

The seal means 82 of the present invention for joining the proximal edges 64 to the side flaps 58 are shown in FIG. 2. The seal means 82 provide a seal along the proximal edge 64 to present a barrier to the wicking of liquids through the topsheet 38. While the topsheet 38 or the absorbent core 44 may extend beyond the seal means 82, protection against leakage of liquids emanating from the edges of the absorbent core 44 or wicking along the topsheet 38 may be enhanced by making the topsheet or the absorbent core not extend beyond the proximal edge 64. The seal means 82 may be any means for securing the proximal edges 64 to the side flaps 58 such as adhesives, heat/pressure sealing, ultrasonic bonding, or any other means or methods as are known in the art. The seal means 78 are preferably three adhesive lines consisting of hot melt adhesive such as adhesives manufactured by Eastman Chemical Products Company of Kingsport, Tennessee and marketed under the trade name Eastbond A-3 or by Century Adhesives, Inc. of Columbus, Ohio and marketed under the trade name Century 5227.

The spacing means 76 for spacing the distal edge 66 away from the liquid-receiving surface 40 is any member which gathers, contracts, stiffens, shortens or otherwise acts on the barrier cuff 62 so as to cause the barrier cuffs 62 to stand up to provide a channel 88 along the barrier cuff 62 that acts as a constraint against the leakage of exudates and a gasketing action about the buttocks of the wearer to provide a snug fit.

As shown in FIG. 1, the spacing means 76 preferably comprises elastic members 77 operatively associated with each of the barrier cuffs 62 adjacent the distal edge 66. The elastic members 77 are preferably secured to the barrier cuff 62 in an elastically contractible condition so that in a normally unrestrained configuration, the elastic members 77 effectively contract or gather the distal edge 66 of the barrier cuff 62. The elastic members 77 can be secured to the barrier cuff 62 in an elastically contractible condition in at least two ways as is discussed in U.S. Pat. No. 3,860,003 entitled "Contractible Side Portion For Disposable Diaper", which issued to Kenneth B. Buell on Jan. 26, 1974, which is incorporated by reference herein. In addition, the length of the elastic member 77 in general is dictated by the diaper design. In the embodiment illustrated in FIG. 1, the elastic member 77 extends along essentially the entire length of the barrier cuff 62 in the crotch region 26, although other lengths are cognizable.

As shown in FIG. 2, the elastic member 77 is operatively associated with the barrier cuff 62 by securing it within the barrier cuff 62 with an elastic attachment means 86. The elastic attachment means 86 should be flexible and of sufficient adhesiveness to hold the elastic member 77 in its stretched condition. While the elastic members 77 may be secured to the barrier cuff 62 adjacent only the ends of the elastic member 77, it is preferable to secure the entire length of the elastic member 77 to the barrier cuff 62. The elastic attachment means 86 herein are preferably glue beads made of hot melt adhesive such as marketed by Findley Adhesives Incorporated, Elmgrove, Wisconsin, as Findley Adhesives 581, although the elastic members 77 may be affixed to the barrier cuff 62 in any of several other ways which are well known in the art. For example, the elastic members 77 may be ultrasonically bonded or heat/pressure sealed into the barrier cuff 62 using a variety of bonding patterns, or the elastic members 77 may simply be glued to the barrier cuffs 62. A more detailed description of the manner in which the elastic members 77 may be positioned and secured to the barrier cuff 62 can be found in U.S. Pat. No. 4,081,301, entitled "Method and Apparatus for Continuously Attaching Discrete, Stretched Elastic Strands to Predetermined Isolated Portions of Disposable Absorbent Products" which issued to Kenneth B. Buell on Mar. 28, 1978, and in U.S. Pat. No. 4,253,461, entitled "Absorbent Brief" issued to Danny L. Strickland and Ronald B.Visscher on Mar. 3, 1981, both of which are incorporated herein by reference. It should be noted that one or more (a plurality of) elastic members 77 can be used to elasticize each barrier cuff 62. Preferably, three elastic members 77 are used to elasticize each barrier cuff 62.

An elastic member 77 which has been found suitable is an elastic strand having a cross section of 0.18 mm by 1.5 mm and made from natural rubber as available from Easthampton Rubber Company of Stewart, Virginia, under the trademark L-1900 Rubber Compound. Other suitable elastic members 77 can be made from natural rubber, such as elastic tape sold under the trademark Fulflex 9411 by Fulflex Company of Middletown, Rhode Island. The spacing elastic member 77 may also comprise any heat shrinkable material as is well known in the art. Other suitable elastic materials may comprise a wide variety of materials as are well known in the art include elastomeric films, polyurethane films, Lycra, elastomeric foams and formed elastic scrim.

In addition, the elastic members 77 may take a multitude of configurations. For example, the width of the elastic members 77 may be varied; the elastic members may comprise a single strand or several parallel or non-parallel strands of elastic material; or the elastic members 77 may be rectilinear or curvilinear.

The spacing means 76 for spacing the distal edge 66 away from the liquid-receiving surface 40 may alternatively comprise several other elements. For example, the barrier cuff 62 may have stiffening means disposed in or on each barrier cuff 62. The stiffening means must be sufficiently stiff so that the distal edge 66 is spaced away from the liquid-receiving surface 40. Suitable materials for the stiffening means include foams, nonwoven fabrics, batting, polyethylene film, formed films, spray glues, foamed elastomerics, polyester, polyurethane, or high loft materials.

The spacing means 76 may also comprise means for shortening the length of the distal edge 66 in comparison to the length of the edges of the diaper 20. The distal edge 66 can be shortened by making a fold or pleat in the distal edge 66. This fold or pleat is secured by any of the holding means well known to those of ordinary skill in the art, such as adhesives or heat sealing. Alternatively, a section may be cut out of the distal edge and the resultant edges brought together to form a butt or lap joint. The distal edge 66 may also be shortened by attaching a length of the distal edge 66 to the topsheet 38 at a position different from where the distal edge 66 would lie when the diaper 20 is in a flattened out condition. Other shortening techniques as are known in the art may also be used.

The first closing means 78 and the second closing means 80 for securing the first end 72 and the second end 74, respectively, of the barrier cuff 62 closed are shown in FIGS. 1, 3 and 4. The closing means provide a more comfortable fit for the wearer and secure the distal edges 66 of the barrier cuff 62 in the proper position to form an inflected barrier cuff. In a preferred embodiment as shown in FIG. 1, the first closing means 78 are disposed in the first waist region 22 in a first closure zone 92 and the second closing means 80 are disposed in the second waist region 24 in a second closure zone 94. The remaining portions of the distal edges 66 are preferably not secured to any underlying structure of the diaper 20 so that the distal edges 66 are left freely openable. In a preferred embodiment, the length of the first closure zone 92 is from about 35 mm (about 1.5 inches) to about 75 mm (about 3 inches), preferably about 63 mm (about 2.5 inches), while the length of the second closure zone 94 is from about 75 mm (about 3 inches) to about 125 mm (about 5 inches), preferably about 114 mm (about 4.5 inches). Thus, the second closing means 80 preferably extends longitudinally inward a length greater than the length that the first closing means extends longitudinally inward such that the second closure zone 94 is preferably longer than the first closure zone 92. This construction is preferred so as to create a snug fit about the buttocks of the wearer to especially prevent leakage of loose fecal material.

While each of the closing means may comprise any of several securement means as are known in the art such as ultrasonic bonds or heat/pressure bonds or seals using a variety of bonding patterns, or adhesives and/or glues, the closing means are preferably adhesive beads consisting of hot melt adhesive such as manufactured by Eastman Chemical Products Company of Kingsport, Tennessee and marketed under the trade name Eastobond A-3 or by Century Adhesives, Inc. of Columbus, Ohio and marketed under the trade name Century 5227.

The diaper 20 is preferably applied to a wearer by positioning the second waist region 24 under the wearer's back and drawing the remainder of the diaper 20 between the wearer's leg so that the first waist region 22 is positioned across the front of the wearer. (It should be noted that the first waist region 22 may alternatively be placed under the wearer's back and the second waist region 24 brought up about the wearer, however, this method does not provide all of the advantages discussed herein.) The ends of the tape tab fasteners 56 are then secured preferably to outwardly facing areas of the diaper 20. In this manner, the stand-up portion of the barrier cuffs 62 should be disposed in the "no motion" zone of the wearer in the crotch region 26 and the flipped out portion be positioned in less than about 50% of the length of the diaper 20, preferably so as to be disposed in only the second waist region 24, so as to provide a gasketing action about the buttocks of the wearer.

As illustrated in FIG. 4, a preferred tape tab 56 is anchored to the diaper 20 to create a manufacturer's end 102 (i.e., that attachment of the tape tab to the diaper 20 made during manufacture of the diaper 20). The tape tab has another element which forms the user's end 104 (i.e., that joint made by the person in securing the diaper to the wearer). Thus, the preferred tape tab 56 has at least three elements, a first fixed portion 106 having a first surface 108 and a second surface 110, a second fixed portion 112 having a first surface 114 and a second surface 116, and a connective portion 118 having a first surface 120 and a second surface 122. The first fixed portion 106 is that portion of the tape tab 56 which is joined to the diaper 20 by securing the first fixed portion 106 to the barrier cuff 62. The second fixed portion 112 is that portion of the tape tab 56 which is attached to the backsheet 42. The first fixed portion 106 and the second fixed portion 112 thus form the manufacturer's end 102 of the tape tab 56. The connective portion 118 is that portion of the tape tab 56 which is attached to another portion of the diaper, generally the backsheet 42, by the user when securing the diaper on the wearer. The connective portion 118 thus forms the user's end 104. Additionally, the second surface 116 of the second fixed portion 112 and the second surface 122 of the connective portion 118 form the backing surface 124 of the tape tab 56 while the first surface 108 of the first fixed portion 106 and the first surface 120 of the connective portion 118 form the fastening surface 126 of the tape tab 56.

The preferred Y-shaped tape tab can be constructed in several ways. The first fixed portion 106, the second fixed portion 112 and the connective portion 118 can each be separate tapes which meet and are joined adjacent the longitudinal edge 30 of the diaper 20 in an area of joinder. The more practical structure for the tape tab is one in which the connective portion 118 and either the first fixed portion 106 or the second fixed portion 112 is a unitary strip of tape material. If the connective portion 118 is unitary with a second fixed portion 112 as shown in FIG. 4, then the first fixed portion 106 is a separate element which is attached to the combined connective portion and the second fixed portion adjacent to the longitudinal edge 30 of the diaper 20 at an area of joinder.

FIG. 4 also shows tab attachment means for securing the tape tab to the diaper 20. These tab attachment means are any of those attachment means which provide an adequate bond, and preferably are any of the pressure-sensitive adhesives well-known to those of ordinary skill in the adhesive art. The second surface 110 of the first fixed portion 106 is affixed to the barrier cuff 62 by a first tab attachment means 128. The first surface 114 of the second fixed portion 112 is attached to the backsheet 42 by a second tab attachment means 130. The connective portion 118 has an adhesive securement means 132 associated with it on the first surface 120. This adhesive securement means 132 forms a joint between the connective portion 118 and the backsheet 42 during use. Since the connective portion 118 and the second fixed portion 112 are preferably unitary as shown in FIG. 4, the adhesive securement means 132 and the second tab attachment means 130 are generally the same element coated onto the unitary structure in a continuous manner.

As shown in FIG. 4, the first fixed portion 106 is secured to the barrier cuff 62. By securing the first fixed portion 106 to the barrier cuff 62, the diaper 20 is provided with a circumferential closure in the closure line of force to provide an effective leg anchoring at the top of the wearer's leg. Such a feature is especially effective when the distal edges 66 of the barrier cuff 62 are angled away from each other. The inverted barrier cuff provides a snug contoured fit around the buttocks while anchoring the barrier cuff at the leg.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A unitary disposable absorbent article having a first waist region, a second waist region, a crotch region disposed between said first waist region and said second waist region, longitudinal edges, and end edges, the disposable absorbent article comprising:

a liquid pervious topsheet;

a liquid impervious backsheet associated with said topsheet;

an absorbent core positioned between said topsheet and said backsheet, said absorbent core having side edges and waist edges;

a side flap extending outwardly from each side edge of said absorbent core in at least the crotch region;

a barrier cuff disposed adjacent each longitudinal edge of the absorbent article, each of said barrier cuffs having a proximal edge and a distal edge, said proximal edge being joined to said side flap;

spacing means operatively associated with said barrier cuff for spacing said distal edge away from said topsheet of the absorbent article;

first closing means for securing a portion of said distal edge of said barrier cuffs to the absorbent article inboard of said proximal edge and over said absorbent core, said first closing means being disposed in said first waist region of the absorbent article in a first closure zone which first closure zone is disposed inboard of said side flap and over said absorbent core; and second closing means for securing a portion of said distal edge of said barrier cuffs to the absorbent article outboard of said proximal edge, said second closing means being disposed in said second waist region of the absorbent article in a second closure zone.

wherein said barrier cuffs are inverted in said second waist region relative to said first waist region; and fastening means for securing the absorbent article on the wearer, said fastening means being positioned in said second waist region of the absorbent article which fastening means is secured to said distal edge of said barrier cuff and secures said distal edge to said topsheet to provide the absorbent article with a closure around the circumference of the wearer's waist and an effective means for anchoring the distal edge of the barrier cuff at the top of the wearer's leg which utilizes the same forces utilized to secure the article on the wearer to also provide the barrier cuff with a snug contoured fit around the wearer's buttocks.

2. The absorbent article of claim 1 wherein said fastening means comprises a tape tab having a manufacturer's end secured to the absorbent article, and a user's end.

3. The absorbent article of claim 2 wherein said manufacturer's end comprises a first fixed portion and a second fixed portion such that said first fixed portion is secured to said barrier cuff.

4. The absorbent article of claim 1 wherein said distal edges of said barrier cuffs are laterally spaced form each other from about 150 mm to about 200 mm in said second waist region.

5. The absorbent article of claim 4 wherein said distal edges of said barrier cuffs are laterally spaced from each other from about 75 mm to about 100 mm in said crotch region.

6. The absorbent article of claim 3 wherein said tape tab is Y-shaped and said second fixed portion of said manufacturer's end of said fastening means is secured to the backsheet of the absorbent article.

* * * * *